US009358387B2

(12) United States Patent
Suwito et al.

(10) Patent No.: US 9,358,387 B2
(45) Date of Patent: Jun. 7, 2016

(54) LEADLESS PACEMAKER

(71) Applicant: BIOTRONIK SE & Co. KG, Berlin (DE)

(72) Inventors: Wantjinarjo Suwito, West Linn, OR (US); Andrew Lynch, Vancouver, WA (US)

(73) Assignee: BIOTRONIK SE & Co KG, Berlin (DE)

( * ) Notice: Subject to any disclaimer, the term of this patent is extended or adjusted under 35 U.S.C. 154(b) by 110 days.

(21) Appl. No.: 14/227,112

(22) Filed: Mar. 27, 2014

(65) Prior Publication Data
US 2014/0303704 A1    Oct. 9, 2014

Related U.S. Application Data

(60) Provisional application No. 61/809,897, filed on Apr. 9, 2013.

(51) Int. Cl.
*A61N 1/05* (2006.01)
*A61N 1/375* (2006.01)
*A61N 1/372* (2006.01)

(52) U.S. Cl.
CPC ............... *A61N 1/059* (2013.01); *A61N 1/057* (2013.01); *A61N 1/3756* (2013.01); *A61N 1/37205* (2013.01)

(58) Field of Classification Search
CPC  A61N 1/05; A61N 1/0573; A61N 2001/0578
See application file for complete search history.

(56) References Cited

U.S. PATENT DOCUMENTS

| 3,835,864 | A |  | 9/1974 | Rasor et al. |
| 5,545,201 | A | * | 8/1996 | Helland ............... A61N 1/0573 600/377 |
| 2010/0114280 | A1 | * | 5/2010 | Hill ...................... A61N 1/0573 607/116 |
| 2011/0251660 | A1 |  | 10/2011 | Griswold |
| 2012/0116489 | A1 |  | 5/2012 | Khairkhahan et al. |
| 2012/0158111 | A1 | * | 6/2012 | Khairkhahan ......... A61N 1/375 607/127 |
| 2012/0172690 | A1 |  | 7/2012 | Anderson et al. |

OTHER PUBLICATIONS

European Search Report and Notes to the European Search Report on European Patent Application No. EP 14 16 2987, dated Jun. 11, 2014 (6 pages).

* cited by examiner

*Primary Examiner* — Christopher D Koharski
*Assistant Examiner* — Michael D Abreu
(74) *Attorney, Agent, or Firm* — Buchanan Ingersoll & Rooney PC

(57) ABSTRACT

Leadless pacemaker, including a hermetic housing, a pacing electrode on a distal portion of the housing, an electronics package in the housing and configured to generate/deliver pacing pulses to the electrode, and a fixation mechanism on the housing distal portion. The fixation mechanism includes at least one deformable hook-shaped thin fixation wire having an attachment portion fixedly attached at the distal portion of the housing and a free end portion which is angled or bent with respect to the attachment portion such that it extends essentially in conformity, but with a small spacing, to a neighbored surface portion of the housing such that the free end portion engages with heart tissue onto which the distal portion is pressed upon rotation of the pacemaker in the direction in which the free end portion extends from the attachment portion, and disengages upon rotation of the pacemaker in the opposite direction.

17 Claims, 3 Drawing Sheets

LEADLESS PACEMAKER

CROSS-REFERENCE TO RELATED APPLICATIONS

This patent application claims the benefit of U.S. Provisional Patent Application No. 61/809,897, filed on Apr. 9, 2013, which is hereby incorporated by reference in its entirety.

TECHNICAL FIELD

The present disclosure relates generally to leadless cardiac pacemakers and, more particularly, to features and methods by which they are attached to bodily tissue, namely, heart tissue. More specifically, the present disclosure relates to features for attaching a leadless cardiac pacemaker to heart tissue with a radial fixation mechanism.

BACKGROUND

Cardiac pacemakers provide an electrical stimulation of the heart when its own natural stimuli generation and/or conduction system fails to provide synchronized atrial and ventricular contractions at rates sufficient for a mammal's health. Furthermore, cardiac pacemakers may provide electrical overdrive stimulation to suppress or convert tachyarrhythmia.

Whereas most types of cardiac pacemakers comprise a pacemaker housing for an electronics package, which is implanted far from the heart, and a pacemaker lead which connects the housing with a pacing electrode, which is arranged within the heart, specific pacemakers have been developed, the housing of which is to be arranged in the heart. Such pacemakers are known as leadless pacemakers, as they do not require a pacing lead for connecting the electronics package to the pacing electrode. Instead, the pacing electrode is disposed on a distal portion of the housing. The leadless type pacemaker can solve typical problems with pacing leads, e.g., that they become a site of infection and morbidity or that they can become defective, thus deteriorating the pacemaker's performance or even blocking the delivery of pacing pulses at all.

Both in standard pacemaker arrangements and in leadless pacemakers, it is essential for their function to provide reliable and durable contact between the pacing electrode and the bodily tissue (e.g., heart tissue). Hence, for many years, considerable efforts have been made to develop suitable fixation mechanisms. Many such mechanisms, which are based on different fixation principles, have been implemented in commercial pacing lead configurations or leadless pacemakers, respectively. For example, a recent development regarding a leadless pacemaker with radial fixation mechanism is disclosed in U.S. Publication No. 2012/0158111.

The present disclosure is directed toward overcoming one or more of the above-identified problems.

SUMMARY

A leadless pacemaker is provided, comprising a hermetic housing, a pacing electrode disposed on a distal portion of the housing, an electronics package disposed in the housing and configured to generate and deliver pacing pulses to the pacing electrode, and a fixation mechanism arranged on the distal portion of the housing, wherein the fixation mechanism comprises at least one deformable hook-shaped thin fixation wire having an attachment portion fixedly attached at the distal portion of the housing and a free end portion which is angled or bent with respect to the attachment portion such that it extends essentially in conformity, but with a small spacing, to a neighbored surface portion of the housing, such that the free end portion engages with heart tissue onto which the distal portion of the housing is pressed upon rotation of the pacemaker in that direction in which the free end portion extends from the attachment portion, and disengages with the heart tissue upon rotation of the pacemaker in the opposite direction.

A solution for anchoring the pacemaker to the wall of the heart is inspired by the head of a tapeworm. Tapeworms use many small teeth to anchor themselves to the wall of the intestine. One tapeworm species has all of the teeth angled in the same direction allowing it to disengage by moving its head in the opposite direction. The teeth simply slide out of their holes upon rotation in the opposite direction.

The leadless pacemaker of the present invention, at least in some of its embodiments, is advantageous in so far as it can be easily placed by the physician, remain in place for the life of the pacemaker, and can be removed with minimal tissue damage. More specifically, at least in some embodiments, the disclosed fixation mechanism provides for sufficient fixation in a short time after implantation and avoids the problem of the device coming free and causing a pulmonary embolism. Compared to prior passive fixation mechanisms and methods, the fixation mechanism disclosed herein avoids an undue entrenching in scar tissue and enables a sufficiently easy disengagement from that tissue. Compared to prior art combinations of passive and active fixation mechanisms, the inventive mechanism disclosed herein provides a simple fixation means and avoids undue complexity or unduly large dimensions beyond the desired design envelope.

In some embodiments, the inventive fixation mechanism comprises a plurality of separate hook-shaped fixation wires, wherein the fixation wires are arranged such that the free end portions thereof essentially form segments of a closed curve, in particular, a circle or an ellipse, with the ends of each of the wires slightly protruding from the closed curve in a distal direction.

In some alternative embodiments, the fixation mechanism comprises a plurality of separate hook-shaped fixation wires, wherein the fixation wires are arranged such that the free end portions thereof extend obliquely from a virtual inner closed curve, in particular, a circle or an ellipse, accommodating the most inner points of the free end portions of all fixation wires to a virtual outer closed curve, in particular, a circle or an ellipse, accommodating the end tips of all fixation wires.

In at least one further embodiment of the present invention, the or each fixation wire, when a proximal force is exerted on the pacemaker in its state fixed to heart tissue, is deformable such that its end portion bends to adopt to the direction of the proximal force and slides out of the heart tissue without damaging it.

In some further embodiments, the or each fixation wire comprises a central attachment portion and two free end portions, each extending from one end of the central attachment portion. According to a design option, the or each fixation wire or, more precisely, a projection of the or each fixation wire on a plane on which a longitudinal axis of the housing stands orthogonally, is approximately S-shaped.

In at least one further embodiment, the leadless pacemaker of the present invention comprises 2 to 12 fixation wires each having one free end portion.

According to some aspects of embodiments mentioned above, the fixation mechanism of the present invention contains a number of small wire tines which protrude from the header of the device and curve in the tangential direction relative to the diameter of the device. The number of tines is variable, but preferably as few as two tines (or free end portions) is sufficient and as many as 12 tines (or free end portions) is possible depending on device weight, wire diameter, and wire material. However, one skilled in the art will appreciate that the present invention is not limited by the number of tines. The tines engage with the heart tissue by clock-wise rotation of the device during implantation. The tines release from the heart tissue by counter clockwise rotation. If the tines fail to disengage from the heart tissues due to rotation, the device can be removed from the heart by sufficient force at which the tines will deform to slide out of the heart tissue without causing significant damage.

In at least one further embodiment of the present invention, the attachment portion of the or each fixation wire is molded into a resin-molded distal housing portion. More specifically, the housing can comprise a cylindrical or cask shaped body housing most of the electronics package, and the distal housing portion can be conical or bell-shaped, and the or each free end portion of each fixation wire extends tangentially or obliquely close to the end face of the conical or bell-shaped housing portion. In more specific embodiments, the header is bell shaped with a diameter equal to that of the hermetical can, and narrowing down to 4 mm at 2 mm from the end of the can. In some embodiments, the tines exist in a horizontal plane 1.0 to 1.5 mm from the end of the hermetic can. Of course, other distances can be implemented without departing from the spirit and scope of the present invention.

In some embodiments, the or at least one fixation wire forms the only or one pacing electrode. In so far, the pacing electrode can either be one or more of the tines, or a separate post protruding from the header along the long axis of the device.

In at least one embodiment of the present invention, the or each fixation wire is bent two-dimensionally with its attachment portion bent rearward from the or each free end portion. More specifically, the rearwardly bent attachment portion is that portion which is covered with the resin of a resin-molded distal housing portion mentioned further above.

In line with a further embodiment mentioned above, if the fixation wires are those which have two free end portions, for example, between 1 and 6, and preferably 1 or 2, such fixation wires can be provided in the fixation mechanism.

In at least one further embodiment of the present invention, the fixation wires are arranged such that the plane of the closed curve or virtual inner and outer closed curve is between 0.5 and 2.5 mm, and preferably between 1 and 2 mm, proximal with respect to the end face of the distal housing portion or hermetic can, respectively. This is provided as anchoring systems which extend past the current outer diameter of the device during passage through the introducer are unacceptable due to the dimensional constraints that already exist. Therefore, the fixation mechanism disclosed herein fits within the diameter of the device until deployment. Additionally, the fixture must not extend more than 5 mm from the base of the hermetic can during delivery or the fixture must be flexible.

Regarding the material and dimensions of the fixation wires, numerous options are available, as will be appreciated by one skilled in the art. In some embodiments, the or each fixation wire is made from stainless steel, in particular from 316L stainless steel, or Nitinol. Furthermore, the diameter of the or each fixation wire can be between 0.1 and 0.5 mm, and preferably between 0.15 and 0.38 mm. As a matter of fact, the number, thickness, and material of the tines are interdependent and can be chosen by one of ordinary skill in the art according to the dimensions, weight, and specific requirements of the respective pacemaker.

Further features, aspects, objects, advantages, and possible applications of the present invention will become apparent from a study of the exemplary embodiments and examples described below, in combination with the figures, and the appended claims.

DETAILED DESCRIPTION

Figure 1A:
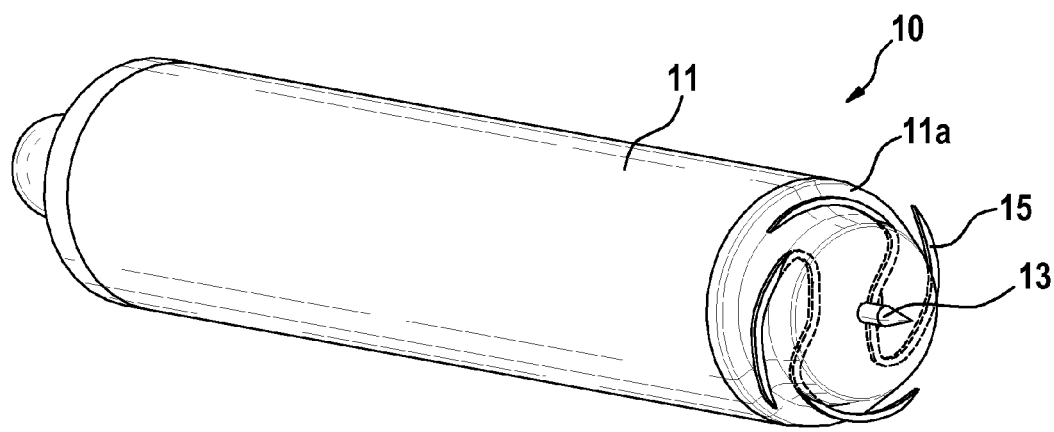
FIGS. 1A, 1B and 1C are showing a perspective view of a leadless pacemaker according to an embodiment of the present invention, a side view of the distal portion thereof, and an end view (distal end) thereof, respectively.
Figure 1B:
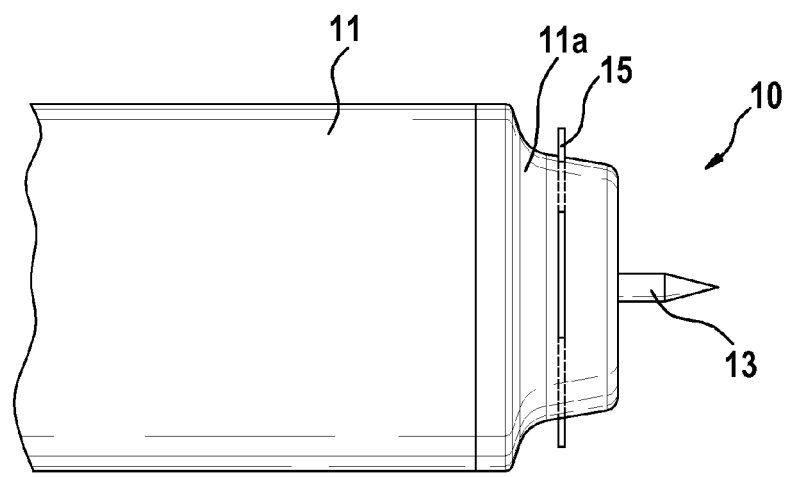
Figure 1C:
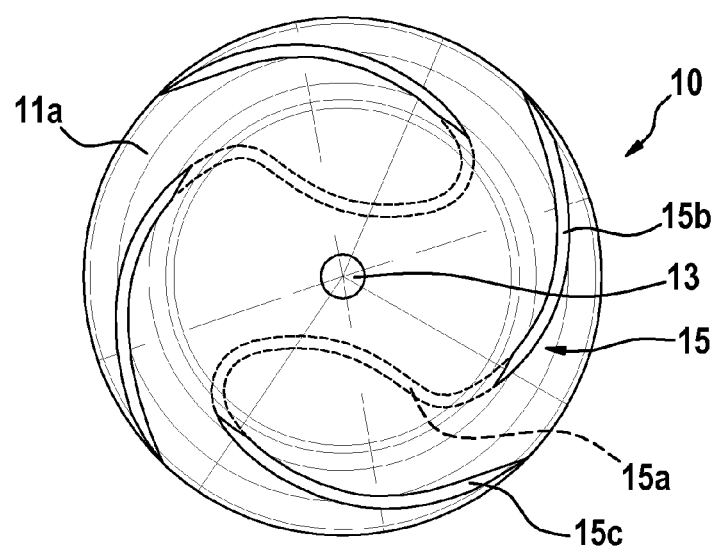

FIGS. 1A to 1C show, as an embodiment of the present invention, a leadless pacemaker 10 which has a basically cylindrical housing 11 for accommodating an electronics package (not shown). The housing 11 has a distal end portion 11a formed as a resin-molded cap which is essentially bell-shaped. In the center thereof, a tip-shaped pacing electrode 13 protrudes distally from the housing 11. Two fixation wires 15 which are essentially S-shaped are, in their central portions 15a, embedded in the resin material of the cap 11a, whereas the end portions 15b, 15c thereof almost tangentially (slightly inclined with respect to the periphery of the cap 11a) extend from both ends of the central portion. In view of its function, the central portion can be designated as attachment portion.

Given that upon clockwise rotation of the pacemaker along its axis the free end portions 15b, 15c would engage with heart tissue against which the distal end 11a of the pacemaker is pressed, the free end portions 15b, 15c could be designated as engagement or fixation portions, respectively. It is to be understood that upon counter-clockwise rotation of the pacemaker, the free end portions 15b, 15c of the fixation wires 15, once in engagement with heart tissue, would gradually disengage from such tissue. On the other hand, the material and dimensions of the fixation wires are selected such that even pulling the pacemaker away from the heart tissue basically along its longitudinal axis would result in disengagement of the free end portions 15b, 15c from the heart tissue, without significant damage thereof.

Figure 2A:
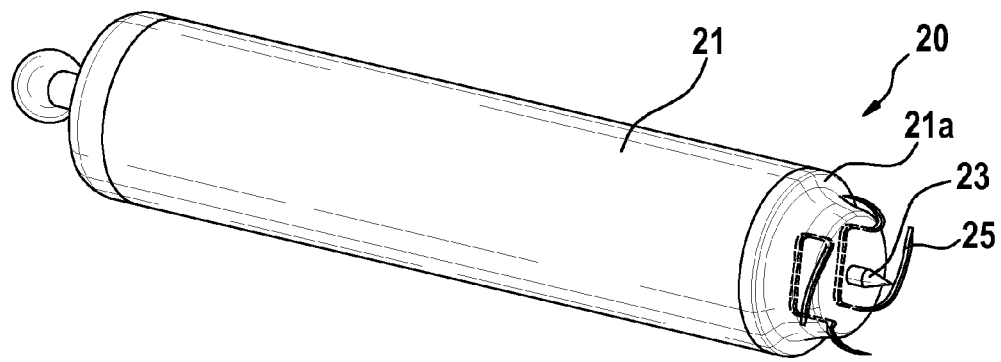
FIGS. 2A, 2B, and 2C are showing a perspective view of a leadless pacemaker according to a further embodiment of the present invention, a side view of the distal portion thereof, and an end view (distal end) thereof, respectively.
Figure 2B:
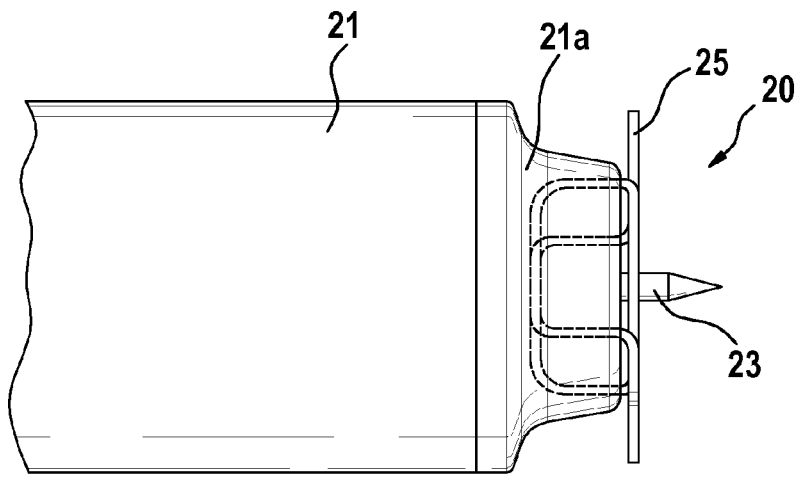
Figure 2C:
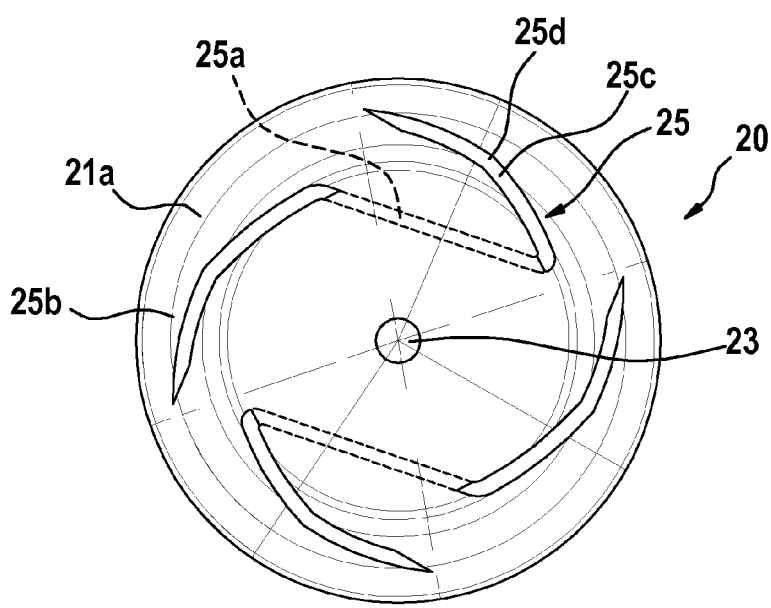

FIGS. 2A to 2C show a leadless pacemaker 20 according to a further embodiment of the present invention. The pacemaker 20 has a cylindrical housing 21 and a distal end portion (resin-molded cap) 21a, the shape and dimensions of which are essentially identical to those of the pacemaker 10 of FIGS. 1A to 1C. The pacemaker 20 has a distally arranged pacing electrode 23 which is formed as a tip electrode and centrally protrudes from the distal end face of the cap 21a. Likewise in the same way as in the first embodiment, two fixation wires 25 are attached to the distal end 21a of the pacemaker by embedding central portions 25a thereof in the resin-molded cap 21a.

However, in this embodiment, the free end portions 25b, 25c extend from both ends of the central attachment portion 25a in a shape which is different from the first embodiment. Firstly, the central portions 25a are, with respect to the plane of extension of the free end portions 25b, 25c, bent rearwardly, i.e., proximally, into the cap 21a, whereas the plane of extension of the free ends is slightly distally from the end face of the cap 21, which at the same time is at the distal end face of the pacemaker 20.

Furthermore, different from the first embodiment, the shape of the fixation wires 25 is more Z-shaped, i.e., the free end portions are, with respect to the central attachment portion 25a, more angled than continuously bent. More precisely, even over the extension of the free end portions 25b, 25c, the fixation wires are not straight but comprise a further kink or angled bend 25d. The overall arrangement of the two fixation wires 25 is such that the respective inner end points of their free end portions are arranged on an inner circle, whereas all ends (sharp tips) of all free end portions 25b, 25c are arranged on an outer circle. The inner circle basically coincides with the periphery of the end face of the cap 21a, whereas the outer circle coincides with the outer periphery of the cylindrical housing 21.

Irrespective of the slightly different shape of the fixation wires, the function of the second embodiment is basically the same as that of the first embodiment. The more distal arrangement of the fixation wires, which at the same time is more distant with respect to the outer surface of the end cap, may result in an easier and more effective engagement into heart tissue and in an even more reliable and durable fixation of the pacemaker to the inner wall of the ventricle.

Figure 3A:
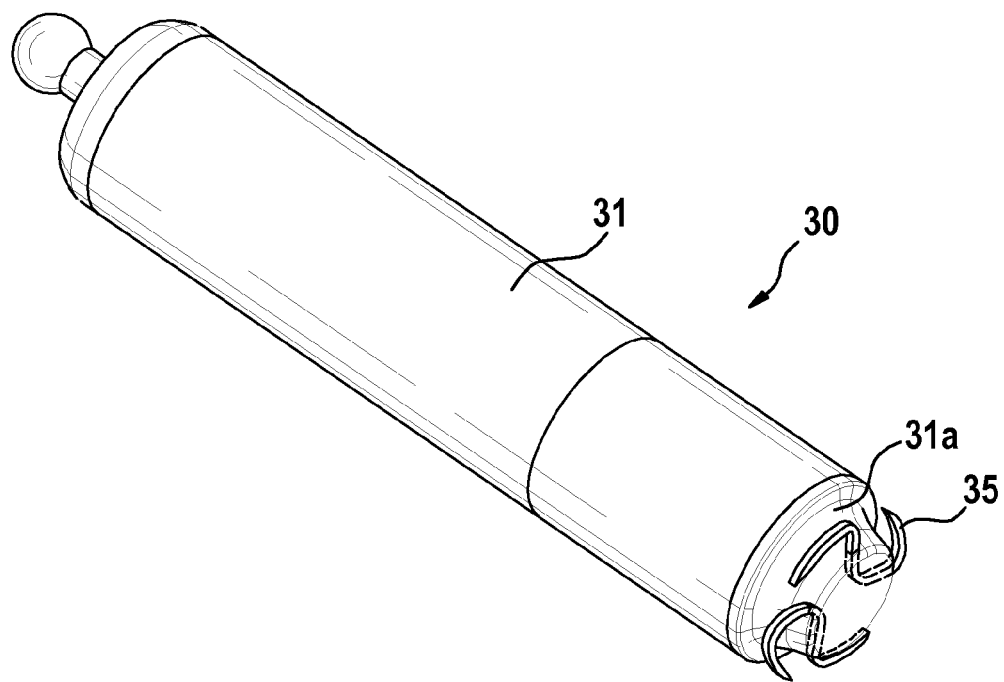
FIGS. 3A and 3B are showing a perspective view and an end view (distal end), respectively, of a leadless pacemaker according to a further embodiment of the present invention.
Figure 3B:
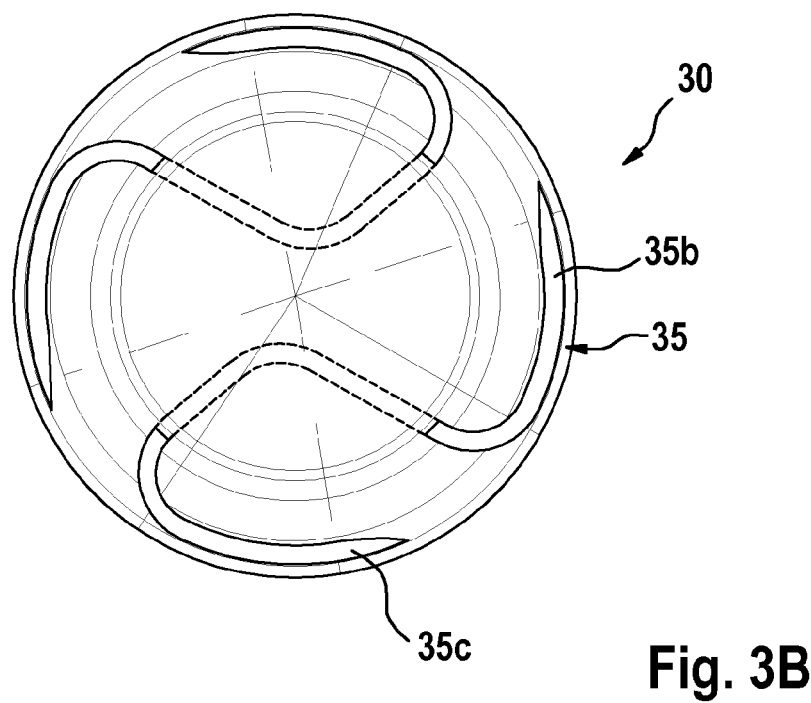

The same holds for a further leadless pacemaker 30 which is illustrated in FIGS. 3A and 3B. As the overall construction and shape of the pacemaker 30 is similar to that of the pacemakers shown in FIGS. 1A to 2C, corresponding parts are designated with corresponding reference numerals and need not be described again. A major difference is that the pacemaker 30 does not have a separate pacing electrode, but that at least one of the fixation wires 35, being connected to the electronics package inside the pacemaker, acts as a pacing electrode.

As a further difference, it should be mentioned that the free end portions 35b, 35c are more smoothly bent and extend more tangentially than those of the pacemaker 20 of FIGS. 2A to 2C. Again, the end tips of all fee end portions 35b, 35c are arranged on an outer circle which coincides with the outer periphery of the housing 31, although being positioned distally from the end 31a of the cylindrical housing 31. As can be seen in FIG. 3B, most of the extension of the free end portions 35b, 35c closely approaches said outer circle, with a very small angle of inclination. This may further reduce damage of the heart tissue, when screwing the distal end of the pacemaker into it, and in so far minimize trauma.

Details pertinent to the present invention, materials and manufacturing techniques are within the skills of one of ordinary skill in the art. Numerous modifications of the embodiments mentioned and described above are possible, within the scope of the appending claims.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given its full breadth thereof. Additionally, the disclosure of a range of values is a disclosure of every numerical value within that range.

We claim:

1. A leadless pacemaker, comprising:
a hermetic housing;
a pacing electrode disposed on a distal portion of the housing:
an electronics package disposed in the housing and configured to generate and deliver pacing pulses to the pacing electrode; and
a fixation mechanism, arranged on the distal portion of the housing, wherein the fixation mechanism comprises at least one deformable hook-shaped thin fixation wire having an attachment portion fixedly attached at the distal portion of the housing and a free end portion which is angled or bent with respect to the attachment portion such that it extends essentially in conformity, but with a small spacing, to a neighbored surface portion of the housing such that the free end portion engages with heart tissue onto which the distal portion of the housing is pressed upon rotation of the pacemaker in a direction in which the free end portion extends from the attachment portion, and disengages upon rotation of the pacemaker in an opposite direction,
wherein the or each fixation wire comprises a one-piece fixation wire comprising a central attachment portion and two free end portions extending from opposite ends of the central attachment portion, and
wherein the or each fixation wire lies in a single plane perpendicular to a longitudinal extent of the housing.

2. The leadless pacemaker of claim 1, wherein the fixation mechanism comprises a plurality of separate hook-shaped fixation wires, wherein the fixation wires are arranged such that the free end portions thereof essentially form segments of a closed curve comprising a circle or an ellipse, and wherein the ends of each of the wires slightly protruding from the closed curve in a distal direction.

3. The leadless pacemaker of claim 2, wherein the fixation wires are arranged such that the plane of the closed curve or virtual inner and outer closed curve is between 0.5 and 2.5 mm proximal with respect to the end face of the distal housing portion.

4. The leadless pacemaker of claim 2, wherein the fixation wires are arranged such that the plane of the closed curve or virtual inner and outer closed curve is between 1 and 2 mm proximal with respect to the end face of the distal housing portion.

5. The leadless pacemaker of claim 2, fixation wires each having one free end portion.

6. The leadless pacemaker of claim 1, wherein the attachment portion of the or each fixation wire is molded into a resin-molded distal housing portion.

7. The leadless pacemaker of claim 6, wherein the housing comprises a cylindrical or cask shaped body housing most of the electronics package, wherein the distal housing portion is conical or bell-shaped, and wherein the or each free end portion of each fixation wire extends tangentially or obliquely close to the end face of the conical or bell-shaped housing portion.

8. The leadless pacemaker of claim 1, wherein the fixation mechanism comprises a plurality of separate hook-shaped fixation wires, wherein the fixation wires are arranged such that the free end portions thereof extend obliquely from a virtual inner closed curve comprising a circle or an ellipse, accommodating the most inner points of the free end portions of all fixation wires to a virtual outer closed curve comprising a circle or an ellipse, accommodating the end tips of all fixation wires.

9. The leadless pacemaker of claim 1, wherein the or each fixation wire, when a proximal force applied in a direction along a longitudinal axis of the housing is exerted on the pacemaker in its state fixed to heart tissue, is deformable such that its two free end portions bend to adopt to the direction of the proximal force and slide out of the heart tissue without damaging it.

10. The leadless pacemaker of claim 1, wherein a projection of the or each fixation wire on a plane on which a longitudinal axis of the housing stands orthogonally is S-shaped.

11. The leadless pacemaker of claim 1, wherein the or each fixation wire is bent two-dimensionally with its attachment portion bent rearward from the or each free end portion.

12. The leadless pacemaker of claim 1, comprising 1 to 6 fixation wires each having two free end portions.

13. The leadless pacemaker of claim 1, comprising 1 or 2, fixation wires each having two free end portions.

14. The leadless pacemaker of claim 1, wherein the or each fixation wire is made from stainless steel or Nitinol.

15. The leadless pacemaker of claim 1, wherein the diameter of the or each fixation wire is between 0.1 and 0.5 mm.

16. The leadless pacemaker of claim 1, wherein the diameter of the or each fixation wire is between 0.15 and 0.38 mm.

17. Leadless pacemaker of claim 1, wherein the or at least one fixation wire forms the only or one pacing electrode.

* * * * *